(12) United States Patent
Chou et al.

(10) Patent No.: US 11,331,365 B2
(45) Date of Patent: May 17, 2022

(54) MULTISPECIFIC PROTEIN DRUG AND LIBRARY THEREOF, PREPARING METHOD THEREFOR AND APPLICATION THEREOF

(71) Applicant: ASSEMBLY MEDICINE, LLC., Shanghai (CN)

(72) Inventors: James Jeiwen Chou, Belmont, MA (US); Liqiang Pan, Zhejiang (CN)

(73) Assignee: Assembly Medicine, LLC, Shanghai (CN)

( * ) Notice: Subject to any disclaimer, the term of this patent is extended or adjusted under 35 U.S.C. 154(b) by 69 days.

(21) Appl. No.: 16/612,004

(22) PCT Filed: Mar. 22, 2018

(86) PCT No.: PCT/CN2018/080058
§ 371 (c)(1),
(2) Date: Nov. 8, 2019

(87) PCT Pub. No.: WO2018/205755
PCT Pub. Date: Nov. 15, 2018

(65) Prior Publication Data
US 2020/0376070 A1  Dec. 3, 2020

(30) Foreign Application Priority Data
May 9, 2017 (CN) .......................... 201710322583.3

(51) Int. Cl.
*A61K 47/54* (2017.01)
*A61K 47/61* (2017.01)
*A61K 38/02* (2006.01)

(52) U.S. Cl.
CPC ............ *A61K 38/02* (2013.01); *A61K 47/549* (2017.08); *A61K 47/61* (2017.08)

(58) Field of Classification Search
CPC ....... A61K 47/56; A61K 47/61; A61K 47/549
See application file for complete search history.

(56) References Cited

U.S. PATENT DOCUMENTS 5,561,043 A * 10/1996 Cantor ............... A61K 47/6949
435/6.16
2003/0027194 A1* 2/2003 Kurz ...................... C12N 15/62
506/9
(Continued)

FOREIGN PATENT DOCUMENTS

CN  1302305 A  7/2001
CN  1558916 A  12/2004
(Continued)

OTHER PUBLICATIONS

Kazane et al. Self-Assembled Antibody Multimers through Peptide Nucleic Acid Conjugation. Journal of the American Chemical Society. Dec. 4, 2012, vol. 135, pp. 340-346. (Year: 2012).*
(Continued)

*Primary Examiner* — Jeffrey E. Russel
(74) *Attorney, Agent, or Firm* — Faegre Drinker Biddle & Reath LLP

(57) ABSTRACT

Provided are a multispecific protein drug and a library thereof, a preparing method therefor and an application thereof. Specifically, a protein drug library is provided and comprises C different protein drug monomers, wherein the protein drug monomer comprises a protein drug component part and a nucleic acid component part connected with the protein drug component part, and the nucleic acid component part of one protein drug monomer establishes a double-stranded paired structure with a nucleic acid component part of at least one different protein drug monomer by means of complementation, thereby constituting a protein drug polymer, wherein C is a positive integer greater than or equal to 2.

10 Claims, 6 Drawing Sheets
Specification includes a Sequence Listing.

$A_N$   Antibody or antibody fragments

〰〰  single-stranded left-handed nucleic acid (e.g. L-DNA, L-RNA)

▫  linker, for linking L-nucleic acids and antibodies

⋮  Nucleic acid base pairing

(56) References Cited

U.S. PATENT DOCUMENTS

2009/0162845 A1 6/2009 Rabbani et al.
2016/0279257 A1* 9/2016 Koussa .................... C12N 9/96

FOREIGN PATENT DOCUMENTS

| CN | 102459346 A | 5/2012 | | |
|---|---|---|---|---|
| CN | 102946906 A | 2/2013 | | |
| WO | WO-2013/028756 A1 | 2/2013 | | |
| WO | WO-2017024238 A1 * | 2/2017 | ............. | C12N 15/11 |

OTHER PUBLICATIONS

Kuijpers et al. Specific Recognition of Antibody-Oligonucleotide Conjugates by Radiolabeled Antisense Nucleotides: A Novel Approach for Two-Step Radioimmunotherapy of Cancer. Bioconjugate Chemistry. 1993, vol. 4, No. 1, pp. 94-102. (Year: 1993).*
Tennila et al. Peptide-Oligonucleotide Conjugates Form Stable and Selective Complexes with Antibody and DNA. Bioconjugate Chemistry. 2008, vol. 19, No. 7, pp. 1361-1367. (Year: 2008).*
International Search Report dated Jun. 13, 2018 for PCT/CN2018/080058.
Written Opinion dated Jun. 13, 2018 for PCT/CN2018/080058.

* cited by examiner

| $A_N$ | Antibody or antibody fragments |
| --- | --- |
| ≡ | single-stranded left-handed nucleic acid (e.g. L-DNA, L-RNA) |
| ○ | linker, for linking L-nucleic acids and antibodies |
| ⋮⋮⋮ | Nucleic acid base pairing |

MULTISPECIFIC PROTEIN DRUG AND LIBRARY THEREOF, PREPARING METHOD THEREFOR AND APPLICATION THEREOF

CROSS REFERENCE TO RELATED APPLICATIONS

This application is a National Stage of International Application No. PCT/CN2018/080058, filed Mar. 22, 2018, which claims benefit of Chinese Application No. 201710322583.3 filed on May 9, 2017.

REFERENCE TO A SEQUENCE LISTING

The instant application contains a sequence listing which has been submitted in ASCII format via EFS-Web and is hereby incorporated by reference in its entirety. Said ASCII copy, created on Nov. 8, 2019, is named 221652_0001_00_US_594455_ST25.txt and is 7,726 bytes in size.

FIELD OF INVENTION

The invention relates to the field of medicine. In particular, it relates to a protein drug library, and methods and uses thereof for constructing multispecific protein drugs (antibodies).

BACKGROUND OF INVENTION

A conventional monoclonal antibody specifically binds to an antigenic site, and its Fc end binds to an Fc receptor on the surface of NK cells, thereby further stimulating immune cell activity. However, it is unable to recruit T cells with great lethality, and thus cannot maximize the activity of the immune system. In addition, traditional monospecific antibodies usually cannot fully utilize or block a signaling pathway based on the antigen or its relevant compensatory pathways by binding to one antigenic site, resulting in unsatisfactory therapeutic effects or prone to drug resistance. For example, antibodies against CD20 recognize different sites on the surface of CD20, so that the activity of these antibodies are significantly different; antibody therapy targeting VEGF on the surface of glioblastoma (GBM) cells can lead to up-regulation of angiopoietin-2 (Ang-2) expression, thereby leading to resistance to anti-VEGF antibodies.

Multispecific antibodies contain specificity for two or more antibodies, they can target epitopes of multiple antigens, or multiple epitopes of an antigen, thus sufficiently blocking downstream pathway of the antigen itself or its interaction with other proteins, thereby improving the therapeutic effect of antibodies and reducing drug resistance. Taking bispecific antibodies as an example, there are currently more than 60 bispecific antibody research and development companies and hundreds of bispecific antibody drugs in research in the world, which are mostly in the form of tumor cell target-T cell recruitment sites (e.g. recruits and activates killer T cells by CD3, recruits natural killer cells (NK cells) by CD16, thereby targeting to kill tumor cells by locally enriched immune cells) and forms of dual target sites (e.g., VEGF-PDGF, VEGF-Ang2, Her2-Her3, reducing potential drug resistance by inhibiting two related signaling pathways). There are also a number of bispecific antibodies targeting multiple epitopes of an antigen, such as MEDI4276 from MedImmune, which is a bispecific antibody-conjugated drug (Bispecific ADC) that targets both the second and fourth domains of Her2. Therefore, multispecific antibodies provide more combinatorial possibilities, synergistic effects, and directly increase the participation of T cells compared to monospecific antibodies; they greatly enhance the immunotherapy effect (such as anti-tumor effect) of antibodies while reducing administration dosage.

The most promising multispecific (bispecific) antibody technology platforms at current stage are mainly BiTE, DART, tandAB, Bi-nanobody, CrossMAB, Triomab etc. These platforms mainly use different antibody engineering techniques to assemble different antibody recognition domains into one protein molecule for multi-specific purposes. For example, BiTE and Bi-nanobody technologies both connect two single-chain (scFv) or nanobody (nanobody) through a flexible peptide-linker peptide while retaining the affinity properties of the two antibody units; Crossmab introduces different mutations in Fc heavy chain regions of two antibodies, so that the heavy chains of the same antibody cannot be assembled due to steric hindrance, while the heavy chains of different antibodies are spatially complementary, and can be smoothly assembled into intact antibody molecules through disulfide bonds. Thus, a bispecific antibody was successfully prepared. However, for assembling two antibodies or fragments into one molecule by protein engineering, it is easy to cause the affinity of the antibody to decrease or be lost. For example, in the case of BiTE, different single-chain antibody combinations need to try different light and heavy chain arrangement order to obtain the optimal bispecific antibody molecules; Crossmab and other full-length antibodies face the problem of light chain mismatch. Although this can be solved by universal light chain technology, it adds more design and screening steps and cannot be directly applied to other bispecific antibodies combinations as a general technique. Multispecific antibodies in the form of full-length antibody such as Triomab, Crossmab, DVD-Ig, and Ortho-Fab-IgG can only be produced in large scale in mammalian cell expression systems (such as CHO, HEK293). And its process is more complicated than antibody fragments (scFv, Fab) and its preparation cost is much higher.

Therefore, there is an urgent need in the art to develop a universal, low-cost, high-yield multispecific antibody preparation technique to construct a protein (e.g., antibody) drug library suitable for individualized precision treatment.

SUMMARY OF INVENTION

The purpose of the present invention is to provide a protein drug library suitable for individualized precision treatment.

Specifically, the present invention provides a platform technology for linking multiple antibody drugs to form a dual or multispecific drug using an L-nucleic acid chain frame. A plurality of antibody drugs can be conveniently and efficiently coupled together to form a library of antibody drugs to be used for individualized precision treatment of diseases.

In the first aspect of the invention, a protein drug library comprising C kinds of different protein drug monomers is provided, wherein the protein drug monomer comprises a protein drug component moiety (or part) and a nucleic acid component moiety to which the protein drug component moiety is linked; and a nucleic acid component moiety of a protein drug monomer and a nucleic acid component moiety of at least one different protein drug monomer may form a double-stranded paired structure by complementation, thereby constituting a multimeric protein drug, wherein C is a positive integer greater than or equal to ($\geq$) 2.

In another preferred embodiment, the multimeric protein drugs are multispecific protein drugs.

In another preferred embodiment, C is any positive integer from 3 to 100,000; preferably, C is from 3 to 10,000; more preferably C is from 5 to 5,000; most preferably C is from 10 to 5,000.

In another preferred embodiment, the multimeric protein drugs are nuclease resistant.

In another preferred embodiment, the nucleic acid component moieties are nuclease resistant.

In another preferred embodiment, the protein drug monomer is nuclease resistant.

In another preferred embodiment, the half-life time H1 of depolymerization of the multimeric protein drug in vivo is greater than the half-life time H2 of the protein drug component alone in vivo.

In another preferred embodiment, the ratio of H1/H2 is from 1 to 100, preferably from 10 to 50, more preferably from 10 to 20.

In another preferred embodiment, the "depolymerization" refers to the dissociation of a multimeric protein drug to form protein drug monomer(s).

In another preferred embodiment, the "in vivo" refers to in vivo in a human or non-human mammal.

In another preferred embodiment, the protein drug component moiety is directly or indirectly linked to the nucleic acid component moiety.

In another preferred embodiment, for a protein drug monomer, the ratio Q (i.e., E2/E1) (Q is molar ratio) of the nucleic acid component moiety E2 to the protein drug component moiety E1 is 10-1, preferably, 4-1, more preferably 2-1, or about 1-1.

In another preferred embodiment, preferably, Q is 2, 1.5, 1.2, 1.1 or 1.05.

In another preferred embodiment, the protein drug is a protein drug administered intravenously.

In another preferred embodiment, the protein drug monomer has the structure shown in formula I:

P-X-L-Y-A-Z    (I);

wherein,

P is a protein drug molecule (i.e., a protein drug component moiety);

X is none or a redundant peptide;

L is a linker molecule;

each of Y and Z is none or a redundant nucleic acid;

A is a nucleic acid sequence selected from the group consisting of: a L-nucleic acid, a peptide nucleic acid, a locked nucleic acid, a thio-modified nucleic acid, a 2'-fluoro-modified nucleic acid, a 5-hydroxymethylcytosine nucleic acid, and combinations thereof;

"-" is a covalent bond;

wherein nucleic acid A of any of the protein drug monomers has at least one complementary pairing region that is partially or fully complementary to a complementary pairing region of nucleic acid A of at least one protein drug monomer in the protein drug library.

In another preferred embodiment, the protein drug molecule P is selected from the group consisting of: an antibody, a ligand of activation receptor or inhibition receptor or other protein, a biologically active enzyme, and combinations thereof.

In another preferred embodiment, the antibody is selected from the group consisting of: a single chain antibody, a nanobody, a Fab, a monoclonal antibody, and combinations thereof.

In another preferred embodiment, the antibody is selected from the group consisting of: an anti-PD-1 single chain antibody, an anti-PD-L1 single chain antibody, an anti-CTLA-4 single chain antibody, an anti-CD-3 single chain antibody, and combinations thereof.

In another preferred embodiment, the antibody is selected from antibodies for the treatment of the following diseases: cancer, autoimmune diseases, immune checkpoints, organ transplant rejection, rheumatoid arthritis, diabetes, hemophilia.

In another preferred embodiment, the target to which the antibody is directed is selected from the group consisting of: CD20, CD19, CD30, HER2, VEGFR, EGFR, RANK, VEGFR2, SLAMF7, GD2, CD33, TNF-a, IL12, IL23, IL6R, IL17, BlyS, CD11a, PD-1, CTLA-4, TIM-3, OX40, CD47, CD3, IL-2R, PCSK9, and GPCR.

In another preferred embodiment, the target to which the antibody is directed is selected from the group consisting of: TNF-a, IL17.

In another preferred embodiment, the target to which the antibody is directed is selected from the group consisting of: CD3, HER2, and PD-1.

In another preferred embodiment, the protein drug molecule P is a wild type or a mutant type.

In another preferred embodiment, the mutation does not affect drug function.

In another preferred embodiment, the mutation comprises introducing one or more cysteine residues at the carboxy terminus (C-terminus) of the antibody.

In another preferred embodiment, X is 0-30 amino acids.

In another preferred embodiment, X is 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids.

In another preferred embodiment, the linker molecule L has a bifunctional linker, which can be coupled with the modified end of the nucleic acid A or Y with a modifying group and the specific linking site of the antibody P or X.

In another preferred embodiment, the reactive groups of the linker molecule L are selected from: maleimide, haloacetyl, thiopyridine.

In another preferred embodiment, the haloacetyl group is selected from: iodoacetyl, bromoacetyl.

In another preferred embodiment, Y is 0-30 nucleotides.

In another preferred embodiment, Y is an L-nucleic acid.

In another preferred embodiment, Y is 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 nucleotides.

In another preferred embodiment, Y is AAAA, AAA or AA.

In another preferred embodiment, Z is 0-30 nucleotides.

In another preferred embodiment, Z is an L-nucleic acid.

In another preferred embodiment, Z is 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 nucleotides.

In another preferred embodiment, Z is AAAA, AAA or AA.

In another preferred embodiment, the nucleic acid A is an L-nucleic acid.

In another preferred embodiment, the nucleic acid A is selected from: DNA, RNA.

In another preferred embodiment, the modifying group is selected from $NH_2$, alkynyl, sulfhydryl (SH), carboxyl (COOH), or a combination thereof.

In another preferred embodiment, the modifying group is $NH_2$.

In another preferred embodiment, the position of the modifying group on the nucleic acid A and/or Y is selected from: the 5' end, the 3' end, any intermediate position.

In another preferred embodiment, there is a transition region of 0-10 nt in length between any two complementary pairing regions in the nucleic acid A.

In another preferred embodiment, the transition region is AAAA, AAA or AA.

In another preferred embodiment, the length of the complementary pairing region is from 5 to 100 nt; preferably from 8 to 50 nt; more preferably from 10 to 30 nt; still more preferably from 12 to 20 nt; most preferably from 10 to 15 nt.

In the second aspect of the invention, it provides a method of assembling a protein drug for personalized treatment, which comprises:

(a) selecting at least two protein drug monomers from the protein drug library of the first aspect of the invention based on pharmaceutical information;

(b) mixing the at least two protein drug monomers to assemble a multispecific protein drug in multimeric form.

In another preferred embodiment, the assembly is to form a double-stranded paired structure by the complementation of the nucleic acid component moiety.

In another preferred embodiment, in the multimeric form of multispecific protein drugs, the nucleic acid component moiety of each protein drug monomer forms a double-stranded paired structure with the nucleic acid component moiety of one or two or three different protein drug monomers.

In another preferred embodiment, the assembly is accomplished by the complementation of nucleic acid component moiety complementary to the single-stranded complementary sequence of the helper nucleic acid molecule (i.e., nucleic acid T) to form a double-stranded paired structure.

In another preferred embodiment, the helper nucleic acid molecule is in a single stranded form.

In another preferred embodiment, the nucleic acid T is a nucleic acid without a conjugated protein drug.

In another preferred embodiment, the nucleic acid T is an L-nucleic acid, or a nucleic acid modified with a modifying group.

In another preferred embodiment, the length of the nucleic acid T is 1-1.5 times the sum of the number of pairs of monomeric nucleic acids in all (b).

In another preferred embodiment, the pharmaceutical information is the protein drug information required for treating a disease of a subject to be treated, including a type, a combination (e.g., antibody combination), and a ratio (the ratio of any two protein drugs P is 1:1 to 1:20) of protein drugs.

In another preferred embodiment, the assembly conditions are: 5-50° C. (preferably 25-40° C.), and reacts for 1-15 minutes (preferably 5-10 minutes).

In another preferred embodiment, the assembly condition is pH 6-9.

In the third aspect of the invention, it provides a multimeric protein drug, which is a polymer formed by D kinds of protein drug monomers which form a double-stranded paired structure by nucleic acid complementation, wherein D is a positive integer greater than or equal to 2; wherein the protein drug monomer comprises a protein drug component moiety and a nucleic acid component moiety to which the protein drug component moiety is linked, and a nucleic acid component moiety of a protein drug monomer and a nucleic acid component moiety of a different protein drug monomer may form a double-stranded paired structure by complementation.

In another preferred embodiment, the nucleic acid component moiety is nuclease resistant.

In another preferred embodiment, the nucleic acid component moiety is selected from: an L-nucleic acid, a peptide nucleic acid, a locked nucleic acid, a thio-modified nucleic acid, a 2'-fluoro-modified nucleic acid, a 5-hydroxymethyl-cytosine nucleic acid, or a combination thereof.

In another preferred embodiment, the protein drug monomer is a protein drug monomer from the protein drug library of the first aspect of the invention.

Wherein D is a positive integer from 2 to 20; preferably D is 2, 3, 4, 5, 6, 7, 8, 9, 10, 11, 12, 13, 14, 15, 16, 17, 18, 19 or 20.

In another preferred embodiment, the multimeric protein drug is a multispecific protein drug.

In another preferred embodiment, the multimeric protein drug is an anti-cancer drug.

In another preferred embodiment, the half-life time H1 of depolymerization of the multimeric protein drug in vivo is greater than the half-life time H2 of the protein drug component alone in vivo.

In another preferred embodiment, the ratio of H1/H2 is from 1 to 100, preferably from 10 to 50, more preferably from 10 to 20.

In the fourth aspect of the invention, it provides a pharmaceutical composition, which comprises:

(i) a multimeric protein drug of the third aspect of the invention as an active ingredient; and (ii) a pharmaceutically acceptable carrier.

In another preferred embodiment, the dosage form of the pharmaceutical composition is selected from an injection, or a lyophilized agent.

It should be understood that, within the scope of the present invention, the technical features specifically described above and below (such as in the Examples) can be combined with each other, thereby constituting a new or preferred technical solution which needs not be described one by one.

The fifth to eighth lanes are bands after assembly, wherein the magnesium ion concentration in lane 5 is 0 mM and the magnesium ion concentrations in lanes 6, 7, and 8 are 1 mM, 2 mM, and 4 mM, respectively.

Figure 4:
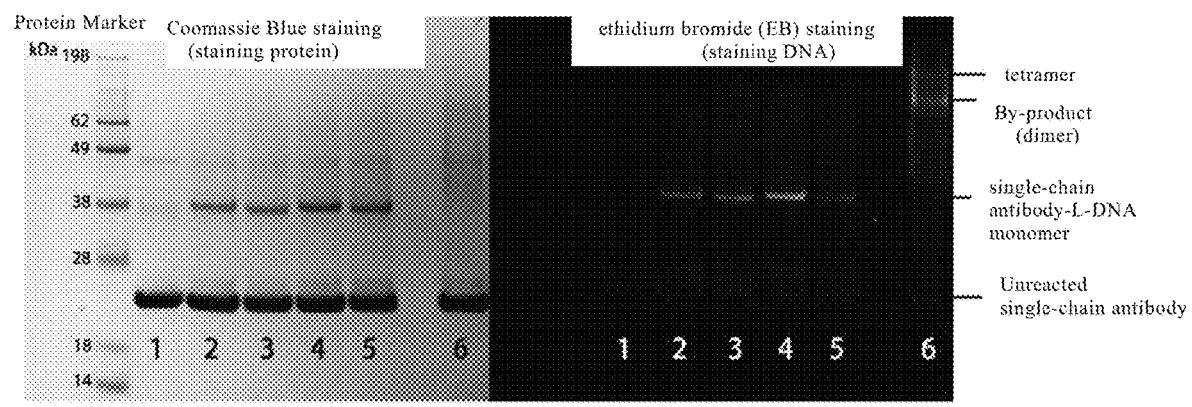

FIG. 4 is a graph showing the results of self-assembly of tetraspecific antibodies. SDS-PAGE gel was stained with ethidium bromide (EB) and coomassie blue successively, to visualize DNA and protein parts respectively. Lane 1 is an unconjugated anti-PD-1 single chain antibody, lane 2 is an anti-PD-L1 single chain antibody conjugated with strand 1 (L-DNA), lane 3 is a anti-PD-L1 single-chain antibody conjugated with strand 2 (L-DNA), lane 4 is an anti-PD-1 single-chain antibody conjugated with strand 3 (L-DNA), and lane 5 is an anti-CD3 single-chain antibody conjugated with strand 4 (L-DNA). Lane 6 is a mixture of four single-chain antibody-L-DNA reaction solutions.

Figure 5:
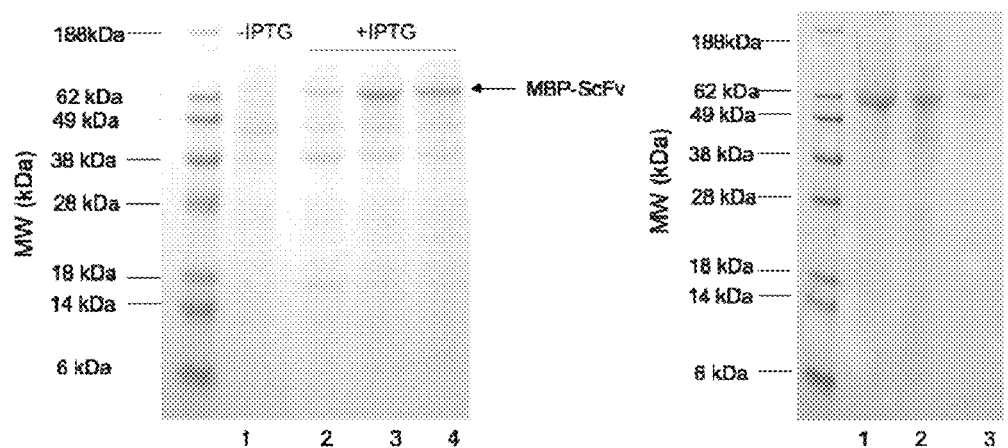

FIG. 5 left is a schematic diagram showing the expression results of MBP-fused single-chain antibody mutants. Lane 1 on the left figure is a control experiment without IPTG induction. Lanes 2, 3, and 4 are protein expression of MBP-anti-CD3 single-chain antibody, MBP-anti-CEA single-chain antibody, and MBP-anti-PDL1 single-chain antibody. The right is a schematic diagram of the solubility of MBP-fused single-chain antibody mutants. Lane 1 on the right figure is a whole bacterial lysate, lane 2 is a soluble component, and lane 3 is an inclusion body component.

Figure 6:
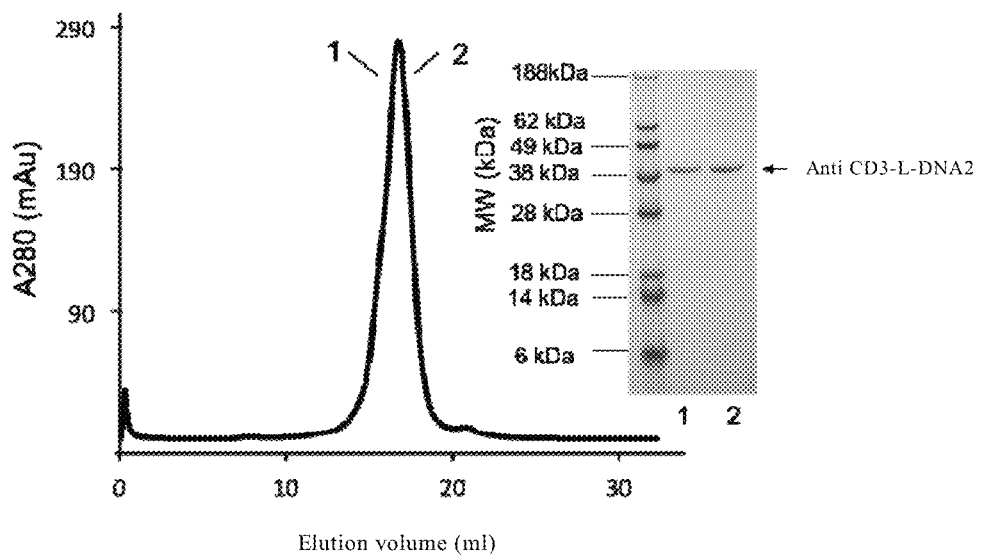

FIG. 6 is a schematic diagram showing the results of purification of anti-CD3-L-DNA2. The figure on the left shows the purification results of a Superdex 200 10/300 GL chromatographic column. The figure on the right shows the purity results of the protein sample by polyacrylamide gel electrophoresis.

Figure 7:
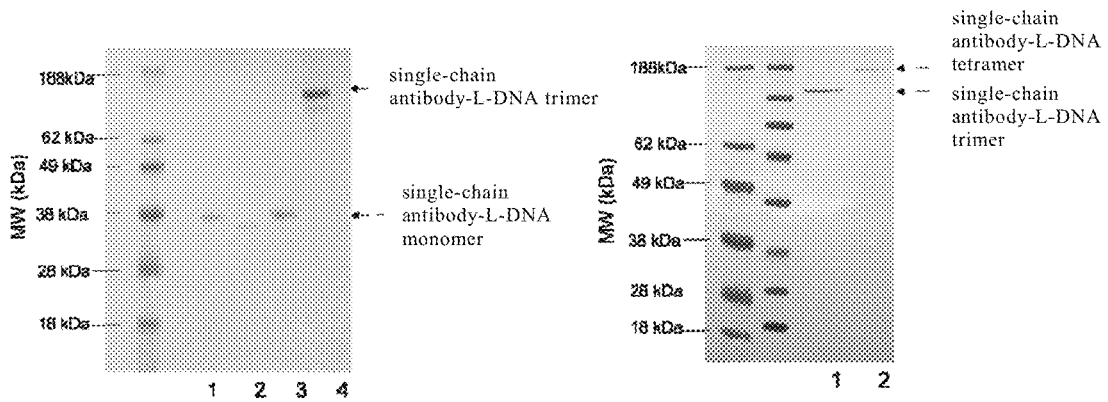

FIG. 7 is a schematic diagram showing the results of self-assembly of multispecific antibodies. The figure on the left is a schematic diagram showing the results of monitoring a multispecific antibody trimer assembly by polyacrylamide gel electrophoresis. Lanes 1, 2, and 3 are anti-CEA-L-DNA1, anti-PDL1-L-DNA2, and anti-CEA-L-DNA3, respectively. Lane 4 is a protein band after self-assembly of three specific antibodies. The figure on the right is a schematic diagram showing the results of monitoring a multispecific antibody tetramer assembly by polyacrylamide gel electrophoresis. Lane 1 is a trimer before reacting with anti-CD3-L-DNA4, and lane 2 is a tetramer after reacting with anti-CD3-L-DNA4.

Figure 8:
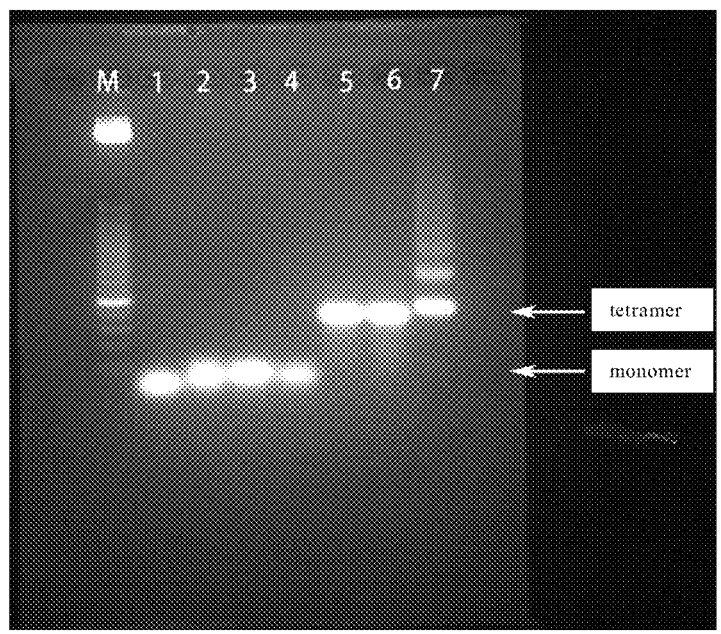

FIG. 8 show that M is a DNA standard with a minimum band of 25 bp and other bands increasing by 25 bp. Lanes 1-4 are four L-DNA (20 uM), respectively, and the loading is 5 ul. Lanes 5 and 6 are assembly methods in which trimers is assembled first at a room temperature and 37° C., respectively, followed by addition of a fourth L-DNA. Lane 7 is an assembly method in which four L-DNAs are directly mixed under conditions of 37° C.

Figure 9:
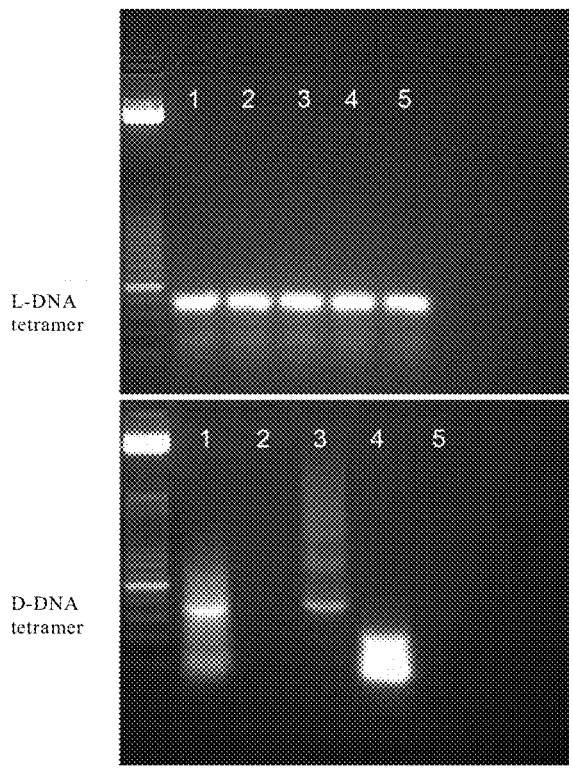

FIG. 9 Lane 1 is an L-DNA tetramer (top) and a D-DNA tetramer (bottom) without any nuclease treatment; lanes 2-5 are L-DNA tetramer sample or D-DNA tetramer sample after treatment by DNAse I, Exonuclease I, T7 DNA endonuclease, and S1 nuclease, respectively. The lowest band of the nucleic acid standard (Marker) is 25 bp, and each band differs by 25 bp.

Figure 10:
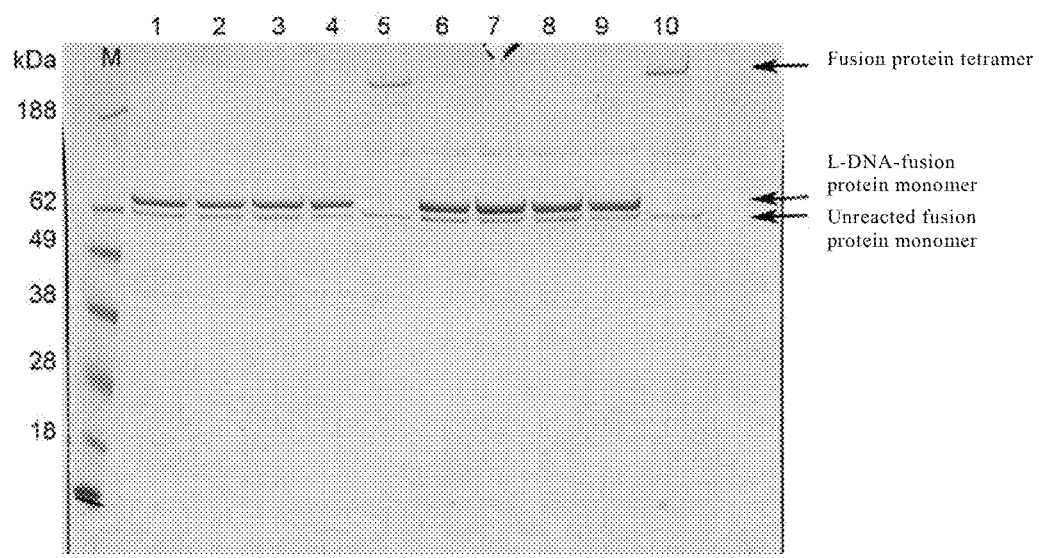

FIG. 10 M is a broad molecular weight protein standard (marker); 1-4 are 1 uM L-DNA-fusion protein monomers, 5 is a 1-4 assembled product; and 6-9 are 2 uM L-DNA-fusion protein monomers, 10 is a 1-4 assembled product.

Figure 11:
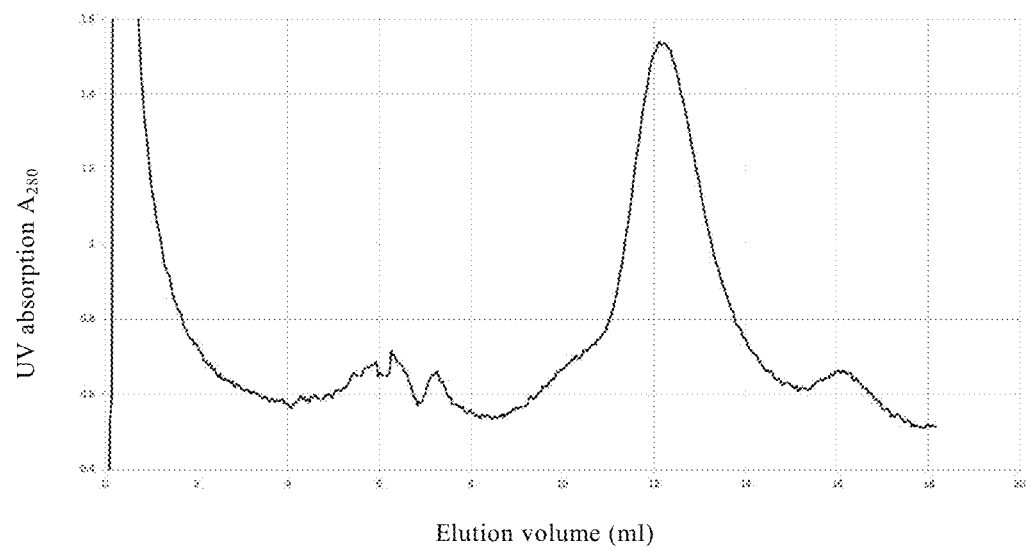

FIG. 11 shows the results of molecular sieve analysis of an L-DNA tetramer scaffold-mediated assembled fusion protein tetramer. The column used is a Superose 6 10/300 molecular exclusion chromatography column (GE).

Figure 12:
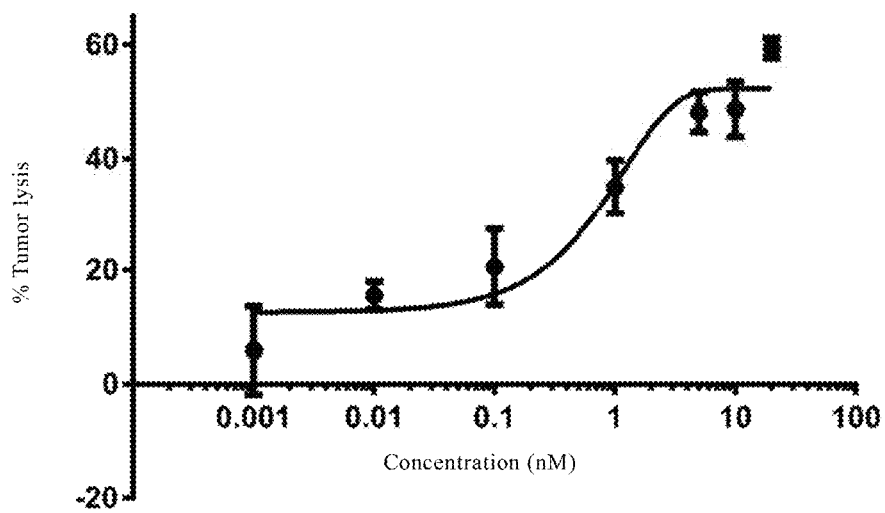

FIG. 12 shows the results of in vitro activity of CEA/PD-L1/CD3 tetraspecific antibodies prepared based on L-DNA scaffold. The colorectal cancer cell line LS174T is CEA positive as a cell model for this in vitro activity assay.

Figure 13:
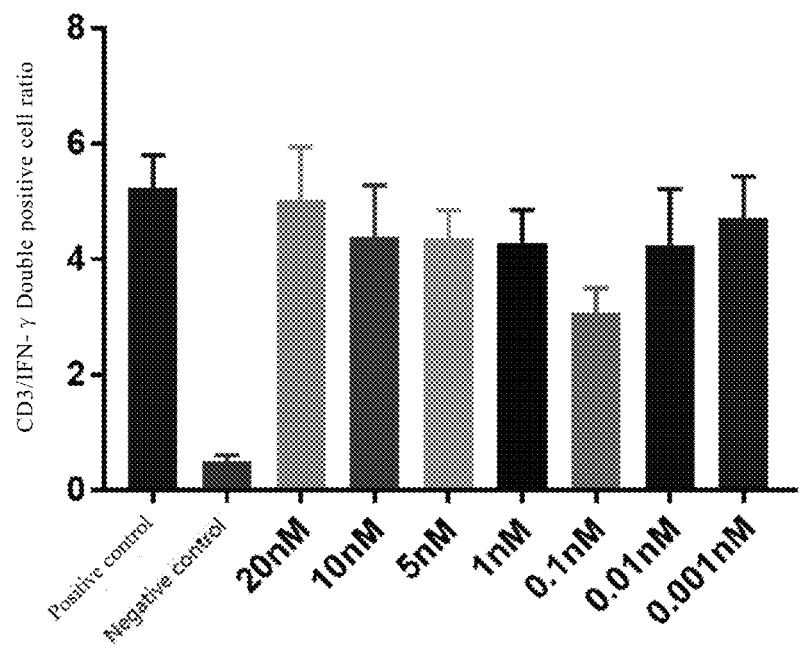

FIG. 13 shows the experimental results of anti-CEA/PD-L1/CD3 tetraspecific antibody in activating T cells. IFN-γ secreted by CD3 positive cells is used as a test subject. The positive control is Dynabeads (fine beads coupled with anti-CD28/CD3 antibodies on the surface and it can efficiently activate T cells), and the negative control is the buffer used for the antibody.

DETAILED DESCRIPTION OF THE INVENTION

Through extensive and intensive researches, the inventors have developed a protein drug library comprising greater than or equal to 2 different protein drug monomers for the first time, the protein drug monomer comprises a protein drug component moiety and a nucleic acid component moiety to which the protein drug component moiety is linked, the nucleic acid component moiety is a nucleic acid resistant to nuclease degradation in vivo (e.g., an L-nucleic acid), and a nucleic acid component moiety of a protein drug monomer and the nucleic acid component moiety of at least one different protein drug monomer may form a double-stranded paired structure by complementation. The corresponding protein drug monomer can be selected from the protein drug library based on needs (such as the condition and diagnosis result of an individual), and multispecific protein drugs (e.g., multispecific antibodies) which target multiple targets and are stable in vivo can be assembled quickly (within 1 minute), efficiently, at low cost, and with high yield. The present invention has been completed on this basis.

Term

Unless otherwise defined, all technical and scientific terms used herein have the same meaning as commonly understood by the ordinary skilled in the art to which this invention belongs. As used herein, the term "about" when used in reference to a particular listed value means that the value can vary from the listed value by no more than 1%. For example, as used herein, the expression of "about 100" includes all values between 99 and 101 (for example, 99.1, 99.2, 99.3, 99.4, etc.).

Although any methods and materials similar or equivalent to those described in this disclosure may be used in the practice or testing of the present invention, the preferred methods and materials are exemplified herein.

As used herein, the terms "protein drug monomer", "protein drug monomer of the present invention", and "drug monomer of the present invention" are used interchangeably.

As used herein, the terms "protein drug library", "protein drug library of the present invention", and "drug library of the present invention" are used interchangeably.

As used herein, the terms "multimeric protein drug of the present invention", "multimeric protein drug", "multispecific protein drug", "multimeric drug protein of the present invention", "multimeric drug protein" and "multimeric protein of the present invention" are used interchangeably.

Protein Drug Library

A protein drug library comprising C different protein drug monomers is provided, wherein the protein drug monomer comprises a protein drug component moiety and a nucleic acid component moiety to which the protein drug component moiety is linked, and a nucleic acid component moiety of a protein drug monomer and the nucleic acid component moiety of at least one different protein drug monomer may form a double-stranded paired structure by complementation, thereby constituting multimeric protein drugs, wherein C is a positive integer greater than or equal to 2.

The library of the present invention further contains at least two or more protein drug monomers, and the preferred protein drug monomer has the structure of formula I as described above.

Since the protein drug monomer of the present invention has a specific structure, they not only can be rapidly assembled into a multimeric form of drug protein, but also the assembled multimeric protein drugs are multispecific. They can simultaneously target a plurality of different targets, and can meet the needs of simultaneously or sequentially targeting multiple targets in the course of disease treatment. In addition, the multimeric protein drugs of the present invention also have unexpected stability in vivo and can be present in the body for a long time and remain active without being rapidly degraded.

For example, in cancer treatment, multiple targets and multiple pathways are often involved, and each patient not only has a distinct etiology, but also has tumor heterogeneity within the same patient. Thus, it is often necessary to use a drug against multiple targets. With the development of personalized therapy or precision treatment technology, there is an urgent need in the art to develop protein drugs (such as multispecific antibodies) that can be rapidly prepared, low in cost, good in targeting, and stable. The library of the present invention meets such demand.

It should be understood that although the library of the present invention contains or consists essentially or wholly of protein drug monomers of the present invention as described above, the library also contains other therapeutic agents, particularly other protein drugs. Representative examples include (but are not limited to): antibodies, compounds, and fusion proteins. For example, a library of the present invention may additionally contain one or more conventional antibodies having therapeutic effects.

It should be understood that the number of protein drug monomers in the library of the present invention is not limited and may be any positive integer C which is greater than or equal to 2. For example, C is any positive integer from 3 to 100,000; C is from 3 to 10,000; more preferably C is from 5 to 5,000; most preferably C is from 10 to 5,000.

Further, in the present invention, the antibody component in the protein drug monomer is not particularly limited, and a representative example is (selected from the following group): a single chain antibody, a nanobody, a Fab, a monoclonal antibody, or a combination thereof.

For the libraries of the present invention, antibodies of various origins can be used to prepare protein drug monomers. An outstanding feature of the libraries of the present invention is that antibody fragments expressed by prokaryotic systems (e.g., *E. coli*) or eukaryotic systems (e.g., yeast, CHO cells) can be used, thereby greatly reducing the cost of production.

Typically, at the time of use, corresponding protein drug monomers can be selected as needed (e.g., the condition and diagnosis results of an individual), and multispecific antibody can be easily completed by nucleic acid complementary frame. For example, at the time of application, the type, amount, or ratio of monomers (e.g., two, three, four, or more than four) are determined according to the target condition of a patient's disease, and then assembled.

During the preparation of multimeric protein drugs, corresponding protein drug monomers which can be paired with and coupled to each other are selected from the library, and after mixing according to the desired antibody ratio, the assembly process can be completed within 1 minute.

In the library of the present invention, the nucleic acid component of protein drug monomers can be designed into a multimer scaffold such as a dimer, a trimer or a tetramer by sequence, thereby achieving the preparation of multispecific antibodies such as trispecific or even tetraspecific antibodies which cannot be easily achieved by conventional antibody engineering.

Once assembled to form a multispecific multimeric protein drug, it can be used to corresponding individual according to purpose of treatment.

Left-Handed Nucleic Acid (L-Nucleic Acid)

L-nucleic acid refers to the mirror image of a naturally occurring right-handed nucleic acid (D-nucleic acid) and it can be divided into left-handed DNA (L-DNA) and left-handed RNA (L-RNA). The left-handed (chiral center) is mainly present in the deoxyribose or ribose portion of the nucleic acid and is mirror-inverted. Therefore, L-nucleic acids cannot be degraded by ubiquitous nucleases (such as exonucleases, endonucleases) in plasma.

Multimeric Protein Drug of the Present Invention and Preparation Thereof

The multimeric protein drug of the present invention is a multimer formed by D protein drug monomers forming a double-stranded paired structure by nucleic acid complementation, wherein D is a positive integer greater than or equal to 2; wherein the protein drug monomer comprises a protein drug component moiety and a nucleic acid component moiety to which the protein drug component moiety is linked, and a nucleic acid component moiety of a protein drug monomer and the nucleic acid component moiety of at least one different protein drug monomer may form a double-stranded paired structure by complementation.

In another preferred embodiment, the nucleic acid component moiety is nuclease resistant.

In another preferred embodiment, the nucleic acid component moiety is selected from: a L-nucleic acid, a peptide nucleic acid, a locked nucleic acid, a thio-modified nucleic acid, a 2'-fluoro-modified nucleic acid, a 5-hydroxymethylcytosine nucleic acid, or a combination thereof.

The multimeric protein drug of the present invention can be formed by, for example, assembly of protein drug monomers of formula I.

Typically, a multimeric protein drug refers to a multimeric antibody (multispecific antibody), such as a bispecific, trispecific, tetraspecific, pentaspecific or hexaspecific antibody. In the present invention, the multimeric antibody of the present invention contains the specificity of two or more antibodies, and can target and bind to epitopes of multiple antigens or multiple epitopes of one antigen, thereby sufficiently blocking the downstream pathway of the antigen itself or its interaction with other proteins, thereby improving the therapeutic efficacy of the antibody while reducing drug resistance.

In a preferred embodiment, the protein drug of the present invention is a multispecific antibody using L-nucleic acids. The research of the present invention shows that a nucleic acid is a double-stranded molecule which can be rapidly and specifically paired. Therefore, if an antibody fragment (such as a single-chain antibody, a nanobody, a Fab, etc.) is conjugated to a nucleic acid single strand, two or more nucleic acid single strands are made to be rapidly paired to form a multimer by designing nucleic acid sequences, thereby guiding antibody fragments to form a multimer too, thereby completing the preparation of a multispecific antibody.

In the present invention, in order to enhance therapeutic effects, it is necessary to employ a protein drug monomer of a specific structure. In a preferred embodiment, the therapeutic effect can be remarkably improved by using left-handed nucleic acids (such as L-DNA, L-RNA, etc.) instead of right-handed nucleic acids (such as D-DNA, D-RNA). One reason is that L-nucleic acids cannot be degraded by exonuclease, endonuclease, etc. present in human body, so multispecific antibody combination mediated by L-nucleic acid (L-nucleic acid) self-assembly will be extremely stable in vivo.

Pharmaceutical Composition

The present invention also provides a composition. In a preferred embodiment, the composition is a pharmaceutical composition comprising the above-described antibody or active fragment thereof or a fusion protein thereof, and a pharmaceutically acceptable carrier. In general, these materials may be formulated in a non-toxic, inert and pharmaceutically acceptable aqueous carrier medium, wherein the pH is generally about 5 to 8, preferably about 6 to 8, although the pH may vary depending on the nature of the substance to be formulated, and the condition to be treated. The formulated pharmaceutical compositions may be administered by conventional routes, including, but not limited to, oral, respiratory, intratumoral, intraperitoneal, intravenous, or local drug delivery.

The pharmaceutical composition of the present invention can be directly used for treatment (e.g., anti-tumor treatment), and thus can be used to prolong half-life of drugs, and further, other therapeutic agents can also be used at the same time.

The pharmaceutical composition of the present invention contains a monoclonal antibody (or a conjugate thereof) of the present invention in a safe and effective amount (e.g., 0.001 to 99 wt %, preferably 0.01 to 90 wt %, more preferably 0.1 to 80 wt %) and a pharmaceutically acceptable carrier or excipient. Such carriers include, but are not limited to, saline, buffer, glucose, water, glycerol, ethanol, and combinations thereof. The pharmaceutical preparation should match the method of administration. The pharmaceutical compositions of the present invention may be prepared into the form of injections, for example, it is prepared by conventional methods using physiological saline or aqueous solutions containing glucose and other adjuvants. Pharmaceutical compositions such as injections, solutions should be prepared under aseptic conditions. The amount of the active ingredient is a therapeutically effective amount, such as about 1 microgram/kg body weight per day to about 10 mg/kg body weight per day. In addition, the polypeptides of the present invention may also be used with other therapeutic agents.

When a pharmaceutical composition is used, a safe and effective amount of an immunoconjugate is administered to a mammal wherein the safe effective amount is generally at least about 10 micrograms per kilogram of body weight and, in most cases, no more than about 8 milligrams per kilogram of body weight, preferably, the dose is from about 10 micrograms per kilogram body weight to about 1 milligram per kilogram of body weight. Of course, the route of administration, the patient's health status and other factors, should be considered for the specific dose, which are within the scope of skills of skilled practitioners.

The Main Advantages of the Present Invention Include:

(1) The multispecific antibody of the present invention is simple and rapid to prepare, and assembly of a plurality of antibodies can be mediated and completed by using left-handed nucleic acid chains in one minute;

(2) The multispecific antibody of the present invention has a broad modification space, and any type of antibody (such as a single chain antibody, a nanobody, a Fab) can be assembled into a multispecific antibody;

(3) In the platform technology for preparing multispecific antibodies of the present invention, various partial antibodies of a multispecific antibody can be prepared separately, and then simple assembly are performed in vitro;

(4) In the platform technology for preparing multispecific antibodies of the present invention, intermediate products (L-nucleic acid-antibody conjugates) of the multispecific antibody of the present invention can be stored, and any combination of antibodies targeting different antigens or epitopes can be flexibly prepared as needed, and an antibody proportion in the multispecific antibody can be adjusted;

(5) An antibody drug library can be constructed based on the platform technology for preparing multispecific antibodies of the present invention, and antibody drugs suitable for individualized precision treatment can be quickly and easily prepared according to given disease and/or pharmaceutical information with low cost and good versatility.

The present invention will be further illustrated below with reference to the specific examples. It should be understood that these examples are only to illustrate the invention, not to limit the scope of the invention. The experimental methods with no specific conditions described in the following examples are generally performed under the conventional conditions (e.g., the conditions described by Sambrook et al., Molecular Cloning: Laboratory Manual (New York: Cold Spring Harbor Laboratory Press, 1989), or according to the manufacture's instructions. Unless indicated otherwise, all percentage and parts are calculated by weight. Unless otherwise stated, the experimental materials used in the following examples are available from commercially available sources.

General Method

1. Design and Preparation of L-Nucleic Acid Chain Frame

According to the present invention, L-nucleic acid chain scaffold is formed by base pairing of two or more L-nucleic acid single strands. The 5' or 3' end of each L-nucleic acid single strand is activated to a group for subsequent modification (such as $NH_2$ or the like), and then one end of a linker (such as SMCC, SM (PEG), SPDP, etc.) is used to conjugate with the activating group on the L-nucleic acid single strand. L-nucleic acids with a linker can be assembled into desired L-nucleic acid chain scaffold. After confirming that the L-nucleic acids with the linker can be successfully self-assembled into a scaffold, the L-nucleic acid single strands with the linker can be conjugate with antibodies respectively for subsequent assembly.

Figure 1:
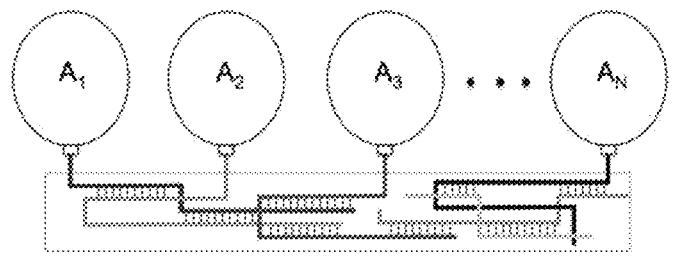
FIG. 1 is a schematic diagram of a multispecific antibody based on self-assembly of L-nucleic acid. It consists of a plurality of antibodies or antibody fragments, multiple self-assemblable L-nucleic acids, and a linker.

FIG. 1 is a schematic diagram showing the configuration of a multispecific antibody prepared by self-assembly of L-nucleic acid, wherein $A_N$ is an antibody or an antibody fragment, such as a single chain antibody, a nanobody, a Fab, etc.; L-nucleic acid scaffold is composed of varying numbers of single-stranded nucleic acids. And one end of the single-stranded nucleic acid has a reactive group modification, such as $NH_2$, etc. The number of single-stranded nucleic acids can be adjusted according to the type of multispecific antibody; for example, tetraspecific antibody requires a minimum number of single-stranded nucleic acids of 4. A linker is used to link the reactive group of a single-stranded nucleic acid to a specific ligation site on an antibody (e.g., an SH group on a mutant cysteine residue).

The L-nucleic acid frame of the present invention can be basically prepared by the following steps.

1.1 Design of L-Nucleic Acid Single Strands that can be Self-Assembled Quickly

Determining the type of multispecific antibody to be prepared (e.g., a trispecific antibody); determining the desired number M of L-nucleic acid single strands based on the number N of antibodies in the multispecific antibody; designing the corresponding number of L-nucleic acid single-stranded sequences, and adjusting the stability of the target nucleic acid scaffold by increasing or decreasing the number of base pairings, and reducing the possibility of non-specific pairing between nucleic acid strands.

Figure 2:
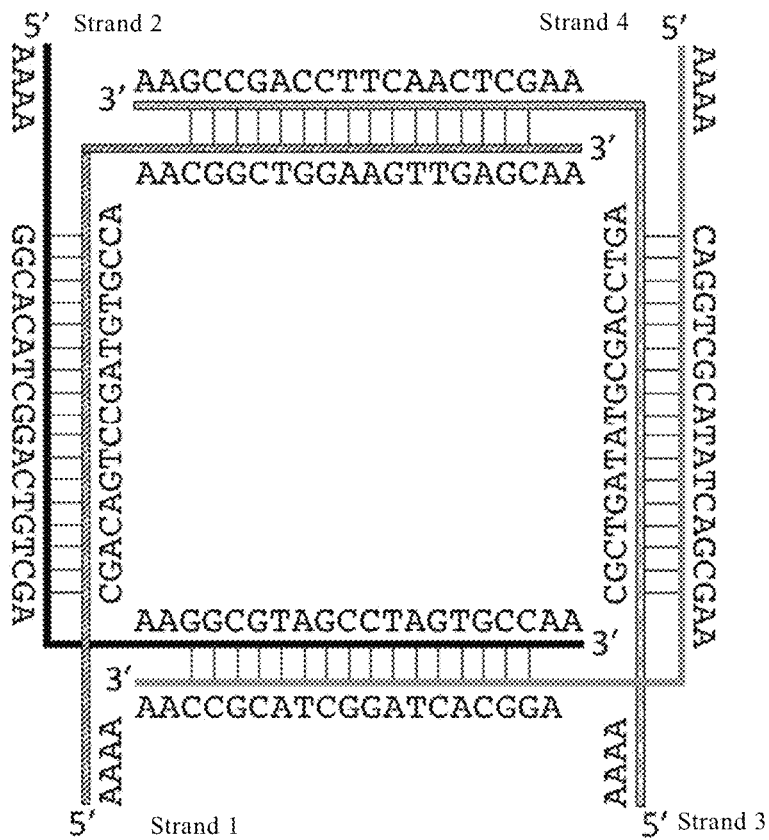
FIG. 2 is a schematic diagram showing the shape and pairing pattern of an L-DNA scaffold of a tetraspecific antibody. Strand 1 corresponds to SEQ ID NO: 1; Strand 2 corresponds to SEQ ID NO: 2; Strand 3 corresponds to SEQ ID NO: 3; and Strand 4 corresponds to SEQ ID NO: 4 (see Example 1).

In accordance with a preferred embodiment of the present invention, to design a tetrameric L-nucleic acid scaffold (M=4), four L-nucleic acids (as shown in FIG. 2) that can be paired according to certain rules are designed. Wherein, any one L-nucleic acid single strand can be specifically complementarily paired with the other two L-nucleic acid single strands, but not paired with the fourth. And Gibbs energy change ΔG of specifically complementary pairing is much lower than that of non-specific pairing. For example, in the preferred embodiment, the Gibbs energy change ΔG of specifically complementary pairing is about −34 kcal per mole (kcal/mole), but for non-specific pairing, which is all greater than −10 kcal per mole (kcal/mole), meaning that tetramer is assembled more easily than non-specific pairwise pairing. The form of tetramer is the most stable in reaction system.

1.2 Activation of L-DNA or L-RNA

Activation of L-nucleic acid includes reactive group modification at its 5' or 3' end and subsequent conjugation with a linker. The reactive group modification can be custom made by nucleic acid synthesis company; the linker generally has a bifunctional group, that is, a reactive group at one end that can couple with nucleic acid, and the other end can be linked to a specific site (such as SH) on an antibody.

According to a preferred embodiment of the present invention, all of the L-nucleic acids constituting the scaffold are added $NH_2$ modification at 5' end, and then the linker, i.e., the bi-heterofunctional group cross-linking agent SMCC (4-(N-maleimide methyl)cyclohexane-1-carboxylic acid succinimidyl ester sodium salt) is used to couple with $NH_2$ on nucleic acid via an amide bond. At this time, the maleimide group at the other end of the linker is in a free state, and can be used for subsequent coupling with thiol group (SH) on an antibody, thereby completing the activation of L-nucleic acids.

1.3 Verification of the Extent of Nucleic Acid Scaffold Polymerization

The extent of nucleic acid scaffold polymerization can be verified by, for example, agarose gel electrophoresis.

According to a preferred embodiment of the present invention, 3% agarose gel electrophoresis is selected to analyze the extent of nucleic acid scaffold polymerization; comparing the size of L-nucleic acid single strand, the size of a scaffold formed by mixing a plurality of L-nucleic acid single strands can be easily derived, and thus the extent of polymerization can be obtained.

Those skilled in the art will appreciate that other L-nucleic acid frames contemplated in the present invention can be similarly prepared in accordance with the above reaction route and methods described in preferred embodiments without limitation.

2. Antibody Selection and Preparation Methods

The antibodies of the present invention are selected based on the use and purpose of multispecific antibodies. If it is used for solid tumor treatment, then multispecific antibodies with high penetrability are required and thus smaller antibody fragments (e.g., single-chain antibodies, nanobodies, etc.) are chosen. If it is used for hematoma, antibodies or antibody fragments can be selected. The specific choice will depend on the use and mechanism of treatment. For preparation of antibody fragments, low-cost expression systems such as *E. coli* or yeast are selected; while a mammalian cell expression system is required for full-length antibodies.

To facilitate conjugation with activated L-nucleic acids, a specific site (e.g., a mutation site, Cys) is introduced into antibody for conjugation with the linker.

According to a preferred embodiment of the present invention, single-chain antibodies against PD-L1/PD-1/CD3 are selected for preparation of a trispecific antibody, wherein PD-1 and CD3 are sites located on the surface of T cells, the main effects are relieving the inhibition of anti-tumor activity and activating CD8-positive T cells respectively. PD-L1 is located on the surface of some tumor cells and prevents T cells from its further killing through interaction with PD-1. Therefore, two anti-PD-L1 single-chain antibodies, one anti-PD-1 single-chain antibody and one anti-CD3 single-chain antibody are used to prepare trispecific antibodies. To make the number of single-chain antibodies used to target tumors and immune cells reach balance, the desired L-nucleic acid scaffold is a tetramer (M=4). A cysteine mutation is introduced at carboxy terminus (C-terminus) of each single-chain antibody for conjugation with SMCC-activated L-DNA single strands. Each single-chain antibody is linked to a different L-DNA single strand, and two anti-PD-L1 single-chain antibodies are at one end of the multispecific antibody, while single-chain antibodies against PD-1 and CD3 are at the other end, facilitating recruitment of T cells to tumor cells.

3. Method for Preparing Antibody-L-Nucleic Acid Complex

First, 5' or 3' end of an L-nucleic acid is modified with $NH_2$ and then the following main preparation methods can be used according to the difference of linkers, wherein one end functional group of the linker is NHS (N-hydroxysuccinimide) or Sulfo-NHS (N-hydroxysuccinimide sulfonate sodium salt) for rapid coupling to the $NH_2$ group at one end of the L-nucleic acid. A linker comprising a bi-heterofunctional group first reacts with the $NH_2$ of an L-nucleic acid. Secondly, after reducing the thiol group on an antibody, the group on the other end reacts with the thiol group to form a stable chemical bond.

3.1 Maleimide. The group of a linker used to couple with thiol groups on an antibody is maleimide. Maleimide reacts rapidly with the free thiol group on an antibody to form a thioether bond. Common linkers are SMCC (4-(N-maleimide methyl) cyclohexane-1-carboxylic acid succinimide ester), SM (PEG) (polyethylene glycol modified 4-(N-maleimide methyl) cyclohexane-1-carboxylic acid succinimide ester and the like.

3.2 Haloacetyl. The group of a linker used to couple with thiol groups on an antibody is a haloacetyl group such as iodoacetyl or bromoacetyl. Halogen ions and thiol group on an antibody can form stable thioether bonds by nucleophilic replacement. Common linkers are SBAP (N-maleimidomethyl [4-bromoacetyl] aminobenzoate), SIAB (N-maleimidomethyl [4-iodoacetyl] aminobenzoate) and the like.

3.3 Pyridyldithiol. The group of a linker used to couple with thiol groups on an antibody is thiopyridine. Thiopyridine can react with free thiol group to form a disulfide bond. Common linkers are SPDP (3-(2-pyridine dithio) propionic acid N-hydroxysuccinimide ester) and the like.

Example 1: Design of a Tetrameric DNA Scaffold

Four L-nucleic acids (see FIG. 2) that are paired in a quadrilateral shape are designed. Wherein, any one L-nucleic acid single strand can be specifically complementarily paired with the other two L-nucleic acid single strands, but not paired with the fourth. And Gibbs energy change ΔG of specifically complementary pairing is much lower than that of non-specific pairing. The Gibbs energy change ΔG of specifically complementary pairing is about −34 kcal per mole (kcal/mole), but for non-specific pairing, which is all greater than −10 kcal per mole (kcal/mole), meaning that tetramer is assembled more easily than non-specific pairwise pairing. The form of tetramer is the most stable in reaction system.

The four L-DNA single-stranded sequences designed according to above principles are as follows (from 5' to 3'):

```
Chain 1 (L-DNA1):
                                          SEQ ID NO: 1
5' AAAA CGACAGTCCGATGTGCC AAA CGGCTGGAAGTTGAGC

AA 3'

Chain 2 (L-DNA1):
                                          SEQ ID NO: 2
5' AAAA GGCACATCGGACTGTCG AAA GGCGTAGCCTAGTGCC

AA 3'

Chain 3 (L-DNA1):
                                          SEQ ID NO: 3
5' AAAA CGCTGATATGCGACCTG AAA GCTCAACTTCCAGCCG

AA 3'

Chain 4 (L-DNA1):
                                          SEQ ID NO: 4
5' AAAA CAGGTCGCATATCAGCG AAA GGCACTAGGCTACGCC

AA 3'
```

The 5' end has an $NH_2$ group modification for coupling with NHS of SMCC. The base sequences following AAAA and AAA are paired with the other two strands, respectively, and the paired Gibbs energy change ΔG of each fraction is about −34 kcal per mole (kcal/mole).

Example 2: Synthesis and Verification of Tetrameric DNA Frame

The 5'-end $NH_2$-modified L-DNA single strand was synthesized by Biotechnology Services, and the sequence of four single strands are shown in Example 1.

L-DNA single strand was dissolved in phosphate buffer (50 mM $NaH_2PO_4$, 150 mM NaCl, pH 7.0) to prepare a mother liquor at a final concentration of 200 uM. SMCC powder was dissolved in dimethyl sulfoxide (DMSO) and a 250 mM SMCC mother liquor was freshly prepared. 10 to 50 fold molar amount of SMCC mother liquor was added to the L-DNA single-strand mother liquor, and the mixture was rapidly mixed and reacted at room temperature for 30 minutes to 2 hours. After the reaction was completed, 1 M Tris-HCl (pH 7.0) with a volume of 10% of the reaction solution was added to the reaction mixture, and the mixture was incubated at room temperature for 20 minutes to stop excess SMCC from continuing to react. After the incubation was completed, 100% absolute ethanol with a volume of 2 times the volume of the reaction solution was added to the reaction mixture, and after mixed evenly, the mixture was placed in a −20° C. refrigerator for 25 minutes to precipitate L-DNA sufficiently. The precipitate was collected by centrifugation (12,000 rpm, 10 min), washed with 1 mL of 70% ethanol, centrifuged at 12,000 rpm for 1 min to remove supernatant, and washed repeatedly for 5 times to remove excess SMCC sufficiently. The remaining white precipitate was naturally dried in air for 5 to 10 min, and then resuspended and dissolved in a phosphate buffer to obtain a SMCC-L-DNA complex (i.e., SMCC-L-DNA single strand).

Figure 3:
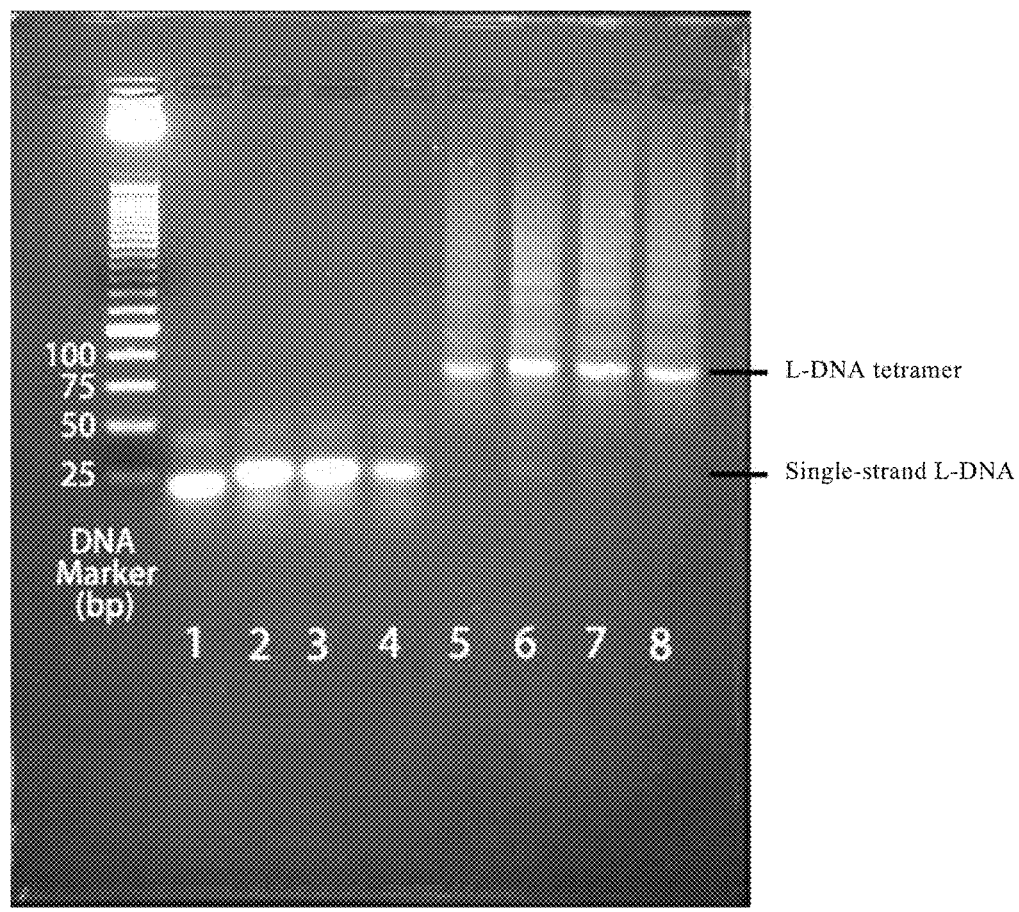
FIG. 3 is a graph showing the results of self-assembly of four SMCC-L-DNAs. 3% agarose gel electrophoresis. The first to fourth lanes are SMCC-L-DNA single strands, wherein the first lane is strand 1, the second lane is strand 2, the third lane is strand 3, and the fourth lane is strand 4.

The concentration of each SMCC-L-DNA single strand was determined. Four kinds of SMCC-L-DNA single strand (in appropriate amount) to be reacted were preheated at 40° C. for 5 min, and then four kinds of SMCC-L-DNA single strands were mixed in an equal molar amount at 40° C. and incubated for 1 min. The reaction system was set with different magnesium ion concentrations to explore the effect of magnesium ion concentration on the formation of scaffold. 0.25 μl SMCC-L-DNA single strand and reaction product were analyzed by 3% agarose gel electrophoresis. As shown in FIG. 3, SMCC-L-DNA single strand has a size of about 25 bp, and the main band formed after mixing was about 100 bp, indicating that the four different SMCC-L-DNA single strands formed a tetramer scaffold, and different magnesium ion concentrations did not affect its self-assembly, showing its extremely high stability.

Example 3: Preparation of Single-Chain Antibody Mutants

A cysteine mutation was introduced at the carboxy terminus of a single chain antibody. Since a disulfide bond exists in a single-chain antibody, and the environment in the cytoplasm of *Escherichia coli* is not conducive to the formation of a disulfide bond, it is necessary to secrete a single-chain antibody into the periplasmic space of *Escherichia coli* to fold and form a disulfide bond.

The gene sequence of anti-PD-1/PD-L1/CD3 single-chain antibody was optimized based on codons preferred by *E. coli*, and NcoI and XhoI restriction sites were added to both ends of the gene, respectively, and then subcloned between NcoI/XhoI sites in a pET22b plasmid. The amino acid sequences of the anti-PD-1/PD-L1/CD3 single chain antibodies are SEQ ID NO: 5, SEQ ID NO: 6, and SEQ ID NO: 7, respectively.

```
amino acid sequence of anti-PD1 single-chain
antibody mutants:
                                          SEQ ID NO: 5
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSAGSGGGGSGGGGSGGGGSEIVLTQSPATLSLSPGERA

TLSCRASQSVSSYLAWYQQKPGQAPRLLIYDASNRATGIPARFSGSGSGT

DFTLTISSLEPEDFAVYYCQQSSNWPRTFGQGTKVEIKC amino acid sequence of anti-PD-L1 single-chain
antibody mutants:
                                          SEQ ID NO: 6
QVQLVQSGAEVKKPGSSVKVSCKTSGDTFSTYAISWVRQAPGQGLEWMGG

IIPIFGKAHYAQKFQGRVTITADESTSTAYMELSSLRSEDTAVYFCARKF

HFVSGSPFGMDVWGQGTTVTVSSAGSGGGGSGGGGSGGGGSEIVLTQSPA

TLSLSPGERATLSCRASQSVSSYLAWYQQKPGQAPRLLIYDASNRATGIP

ARFSGSGSGTDFTLTISSLEPEDFAVYYCQQRSNWPTFGQGTKVEIKC amino acid sequence of anti-CD3 single-chain
antibody mutants:
                                          SEQ ID NO: 7
EVQLQQSGPELVKPGASMKISCKASGYSFTGYTMNWVKQSHGKNLEWMGL

INPYKGVSTYNQKFKDKATLTVDKSSSTAYMELLSLTSEDSAVYYCARSG
```

-continued

```
YYGDSDWYFDVWGQGTTLTVFSGSGGGGSGGGGSGGGGSDIQMTQTTSSL

SASLGDRVTISCRASQDIRNYLNWYQQKPDGTVKLLIYYTSRLHSGVPSK

FSGSGSGTDYSLTISNLEQEDIATYFCQQGNTLPWTFAGGTKLEIKC
```

Due to pelB signal peptide sequence, pET22b plasmid can direct the secretion of single-chain antibodies into periplasmic space. 1 µl of constructed expression vector was transformed into E. coli BL21 (DE3), and transformed BL21 (DE3) single colony was picked into LB medium (containing 100 µg/mL ampicillin), and cultured at 37° C. to OD600=0.7. IPTG was added to induce expression at a final concentration of 1 mM, and culture was continued for 3 to 4 hours at 37° C. Bacteria after completion of expression were collected by centrifugation, resuspended in phosphate buffer (50 mM $NaH_2PO_4$, 150 mM NaCl, pH 7.0), protease inhibitor cocktail (Sigma), and crushed by sonication. DNase I hydrolase was added and incubated on ice for 1 hour. After incubation, bacterial solution was centrifuged at 17,000 rpm for 20 minutes to collect the supernatant. The single-chain antibody in supernatant was purified using a Hitrap Protein L affinity column. After the supernatant was passed through the column at a rate of 0.25 ml/min, a large amount of phosphate buffer (50 mM $NaH_2PO_4$, 150 mM NaCl, pH 7.0) was used to wash the column at 1 ml/min until heteroprotein no longer flowed out (according to UV absorption on AKTA protein chromatography system). Single-chain antibody bound on the column was gradiently eluted with 0-100% elution buffer (50 mM $NaH_2PO_4$, 150 mM NaCl, pH 2.3). The single chain antibody fraction was collected and pH was adjusted to 7.0.

Example 4: Coupling and Purification of Single-Chain Antibody-L-DNA

The purified single-chain antibody is incubated with 10-50 fold molar ratio excess of reducing agent (such as TCEP, DTT, mercaptoethanol, etc.) for 30 min at room temperature. After the incubation, the reducing agent in the reaction system was quickly removed using a PD-10 desalting column while the buffer was replaced with a phosphate buffer (50 mM $NaH_2PO_4$, 150 mM NaCl, pH 7.0). After measuring the concentration of the single-chain antibody, 1-4 fold molar ratio excess of SMCC-L-DNA single strand (prepared in Example 2) was immediately added, mixed evenly, and reacted at room temperature for 1 hour.

Since nucleic acid such as DNA is negatively charged, the single-chain antibody-L-DNA was separated and purified by an anion exchange column (HiTrap Q HP column) to remove unreacted single-chain antibody and excess SMCC-L-DNA single strand. The separation process was carried out by gradient elution with a loading buffer of 50 mM $NaH_2PO_4$, pH 7.0, elution buffer of 50 mM $NaH_2PO_4$, 1 M NaCl pH 7.0, and was gradiently eluted with 0-100% elution buffer. Unreacted single-chain antibody, single-chain antibody-L-DNA, and excess SMCC-L-DNA single-stranded peaks appear successively. Single-chain antibody-L-DNA was collected, concentrated and the buffer was replaced with 50 mM $NaH_2PO_4$, 150 mM NaCl, pH 7.0 using a PD-10 desalting column.

Example 5: Self-Assembly of Multispecific Antibodies

In order to exclude the possibility that the single-chain antibody itself forms a multimer, the single-chain antibody-L-DNA reaction solution in which the conjugation reaction was just completed in Example 4 was used to perform a self-assembly experiment. The single-chain antibody/SMCC-L-DNA reaction ratio in the coupling reaction was 1:0.5, ensuring that there was uncoupled single-chain antibody after the end of the reaction, but it was necessary to remove the unreacted SMCC-L-DNA single strand. Therefore, after the reaction was completed, appropriate amount of Protein L filler was added, and incubated for 10 min, centrifuged at 12000 rpm for 1 min to remove the supernatant, 1 mL of phosphate buffer (50 mM $NaH_2PO_4$, 150 mM NaCl, pH 7.0) was added to wash the filler, centrifuged to remove the supernatant, and repeated this four times. Elution buffer (50 mM $NaH_2PO_4$, 150 mM NaCl, pH 2.3) was added and incubated for 10 min to elute the single-chain antibody adsorbed on the surface of the filler as well as single-chain antibody-L-DNA, and the pH was adjusted to 7.0. Chain 1 (L-DNA1) in Example 1 was coupled to an anti-PD-L1 single chain antibody, chain 2 (L-DNA2) was coupled to an anti-PD-L1 single chain antibody, chain 3 (L-DNA3) was coupled to an anti-PD-1 single-chain antibody, and chain 4 (L-DNA4) was coupled to an anti-CD3 single-chain antibody.

100 µl of the above-mentioned single-chain antibody-L-DNA reaction solution purified by Protein L was preheated at 40° C. for 5 min, and then four equal volumes of single-chain antibody-L-DNA reaction solution were mixed at 40° C., and incubated for 1 min. After the reaction, 30 µl was analyzed by SDS-PAGE. After the electrophoresis, the SDS-PAGE gel was first stained with 2 µg/ml ethidium bromide solution for 20 min, washed three times with ultrapure water and then color developed under ultraviolet light. Bands containing DNA (such as monomer of single-chain antibody-L-DNA, multispecific antibodies) was observed. The same piece of gel was then stained with Coomassie Blue to observe the electrophoresis of all protein samples.

The result is shown in FIG. 4, the single-chain antibody coupled with L-DNA was significantly shifted from the uncoupled single-chain antibody, and only the single-chain antibody coupled with L-DNA was imaged in ultraviolet light. After ethidium bromide (EB) staining, the presence of polymer was observed under an ultraviolet lamp, and they were judged to be a tetramer and a dimer depending on molecular weight. The dimer was present because the amount of anti-CD3 single-chain antibody-L-DNA was significantly less than that of the other three single-chain antibody-L-DNA, so it could not be fully self-assembled into a tetramer, resulting in that three other single-chain antibody-L-DNAs tended to form a dimer non-specifically in two-two combination. After Coomassie brilliant blue staining, it could be seen that after several single-chain antibody-L-DNA was mixed, the band of monomer disappeared, and a blurred band appeared around 150 kDa, which could be judged as a tetramer according to EB staining result. The unreacted single-chain antibody bands did not change, indicating that the formation of a tetramer was due to mutual pairing of L-DNAs. Therefore, the L-DNA tetramer frame can be used to rapidly prepare multispecific antibodies such as tetraspecific antibodies.

Example 6: Expression and Preparation of MBP-Fused Single Chain Antibody Mutant Single-chain antibodies expressed alone in E. coli usually form non-bioactive inclusion bodies. To improve the solubility and biological activity of single-chain antibodies, fusion expression vectors containing maltose-binding protein MBP and three single-chain antibodies (anti-PD-L1/CD3/CEA single-chain antibodies, Seq. No 1, 2 and 3) were constructed to form MBP-ScFv fusion proteins. A TEV cleavage site was introduced between MBP and a single-chain antibody for MBP-tagged excision, and NcoI and XhoI restriction sites were added to both ends of the gene respectively, and then subcloned between NcoI/XhoI sites in a pET22b plasmid.

1 μl of the constructed expression vector was transformed into E. coli BL21 (DE3), and the transformed BL21 (DE3) single colony was picked into LB medium (containing 100 ug/mL ampicillin), and cultured at 37° C. to OD600=0.7. IPTG was added to induce expression at a final concentration of 1 mM, and culture was continued for 12 to 16 hours at 16° C. Small amount of the same amount of bacteria fluid was taken and the protein expression was monitored by polyacrylamide gel electrophoresis. As shown in the left figure of FIG. 5, Lane 1 is a control experiment without IPTG induction, Lanes 2, 3, and 4 are the protein expression of MBP-anti-CD3 single-chain antibody, MBP-anti-CEA single-chain antibody and MBP-anti-PDL1 single-chain antibody, respectively, indicating that the expression of MBP-ScFv fusion protein is stable and the expression level is high in E. coli expression system. The protein has a molecular weight of approximately 69 kDa.

Taking MBP-anti-CEA single-chain antibody as an example, bacteria after expression were collected by centrifugation, resuspended in HEPES buffer (20 mM HEPES+150 mM NaCl, pH=7.4), and protease inhibitor cocktail (sigma), reducing agent mercaptoethanol and DNase I hydrolase were added, crushed by sonication, centrifuged at 39000 g for 40 minutes, and the supernatant was collected as a soluble component. The precipitate was resuspended in the same volume of HEPES buffer as an inclusion body component. Protein soluble condition was monitored by polyacrylamide gel electrophoresis, as shown in the right figure of FIG. 5, wherein lane 1 is the whole bacterial lysate, lane 2 is the soluble component, and lane 3 is the inclusion body component. This indicates that the MBP-ScFv fusion protein is well soluble in the E. coli expression system.

The MBP fusion single-chain antibody mutant was subjected to preliminary purification by nickel column affinity chromatography. The MBP-ScFv fusion protein was added to the nickel column, and effluent was removed after adsorption for 30 minutes. Heteroprotein was eluted with 20 mM and 40 mM imidazole, and target protein was eluted and collected with 400 mM imidazole, waiting for subsequent coupling and purification of single-chain antibody-L-DNA.

Example 7: Coupling and Purification of Single-Chain Antibody-L-DNA

The excess reducing agent mercaptoethanol in the preliminary purified MBP fusion single-chain antibody was quickly removed using a PD-10 desalting column, and 1-4 fold molar ratio excess of SMCC-L-DNA single strand (prepared in Example 2) was added immediately. After mixing evenly, the reaction was carried out at room temperature for 1 hour. Unreacted DNA was removed by amylose resin affinity chromatography, and target protein was bound to the amylose column while unreacted DNA was removed by washing with 10 CV HEPES buffer (20 mM HEPES+150 mM NaCl, pH=7.4). Then, TEV enzyme was added and incubated for 3 hours, allowing the fusion protein to be cleaved on an amylose column. The eluent was a single-chain antibody after excision of MBP fusion protein, and the eluent was collected. Since nucleic acid such as DNA is negatively charged, single-chain antibody-L-DNA was separated and purified using an anion exchange column (HiTrap Q HP column), and TEV enzyme was removed. The separation process was carried out by gradient elution. Loading buffer was 20 mM Tris-Cl+15 mM NaCl, pH=8.5, elution buffer was 20 mM Tris-Cl+1 M NaCl, pH=8.5. It was gradiently eluted with 0-100% elution buffer and TEV enzyme and single-chain antibody-L-DNA peaks appear successively and the single-chain antibody-L-DNA was collected. The single-chain antibody-L-DNA was purified by rapid protein liquid chromatography, and the sample was separated and purified by Superdex 200 10/300 GL column (GE Healthcare) equilibrated with HEPES buffer (20 mM HEPES+150 mM NaCl, pH=7.4). Sample was taken according to ultraviolet absorption A280, while peak position and sample purity was examined by polyacrylamide gel electrophoresis. Taking anti-CD3-L-DNA2 as an example, as shown in FIG. 6, a single-chain antibody-L-DNA conjugate sample having uniform biophysical properties and high purity was finally obtained, and its molecular weight is about 40 kDa.

Example 8: Self-Assembly of Multispecific Antibodies

Chain 1 (L-DNA1) in Example 1 was coupled to an anti-CEA single chain antibody, chain 2 (L-DNA2) was coupled to an anti-PD-L1 single chain antibody, chain 3 (L-DNA3) was coupled to an anti-CEA single chain antibody, and chain 4 (L-DNA4) was coupled to an anti-CD3 single chain antibody. 300 μl of anti-CEA-L-DNA1, anti-PDL1-L-DNA2, anti-CEA-L-DNA3 were pre-heated at 37° C. for 5 min, then three single-chain antibody-L-DNA were mixed at equal volume at 37° C., and incubated for 5 min. After reaction, 30 μl of the reaction solution was taken to monitor the assembly of the antibody by polyacrylamide gel electrophoresis. As shown in the left figure of FIG. 7, lanes 1, 2 and 3 are anti-CEA-L-DNA1, anti-PDL1-L-DNA2, and anti-CEA-L-DNA3 protein band respectively, and lane 4 is a protein band after self-assembling of three specific antibodies, and its protein molecular weight indicates that anti-CEA-L-DNA1, anti-PDL1-L-DNA2, and anti-CEA-L-DNA3 can self-assemble to form a trimer. The trimer was subjected to rapid protein liquid chromatography purification to remove unreacted single-chain antibody-L-DNA monomer. The purified trimer was diluted to a final concentration of 0.1 μM, and an anti-CD3-L-DNA4 was added at equal volume and equal concentration at 37° C. and incubated for 5 min. After reaction, 30 μl of the reaction solution was taken to monitor the assembly of the antibody by polyacrylamide gel electrophoresis. As shown in the right figure of FIG. 7, lane 1 is the trimer before reaction with anti-CD3-L-DNA4, and lane 2 is the tetramer after reaction with anti-CD3-L-DNA4, and its tetramer protein molecular weight is about 168 kDa. Therefore, the above experiments prove that the L-DNA tetramer frame can be used for rapid preparation of multispecific antibodies such as tetraspecific antibodies.

Example 9: Assembly Optimization of Tetrameric DNA Frame

Four L-DNA single strands were dissolved in phosphate buffer (50 mM NaH$_2$PO$_4$, 150 mM NaCl, pH 7.0) to prepare stock solutions having a final concentration of 20 μM. To optimize the assembly of tetrameric DNA scaffold, the assembly process was classified into two ways for comparison: 1. three L-DNA single strands were mixed first, mixed and reacted for 5 minutes at room temperature or 37° C., after waiting for 30 minutes, then the fourth L-DNA single strand was added; 2. four L-DNA single strands were mixed simultaneously, mixed and reacted for 5 minutes at 37° C. After the reaction, 5 µl of each sample was analyzed with a 2% agarose gel.

The result is shown in FIG. 8, when four L-DNAs were simultaneously mixed, the main product was a tetramer, but at the same time there were many non-specific assembly products with high extent of polymerization (lane 7). When three L-DNAs were first mixed and then the fourth L-DNA was added, the reactions at room temperature and 37° C. both resulted in a single tetrameric product without any non-specific bands (lanes 5 and 6). The results indicate that for the assembly of the DNA frame, the assembly mode of first assembling a trimer and then adding the fourth L-DNA is much better than the mode of mixing the four directly.

Example 10: Degradation Resistance Experiment of D-DNA and L-DNA Tetramer Frame

Compared to D-DNA, L-DNA has the advantage of being unable to be degraded by DNase in nature. There are a variety of DNases in human body. To verify whether a L-DNA tetramer scaffold can be degraded or depolymerized by DNase, DNAse 1, T7 endonuclease, S1 nuclease, exonuclease I were selected to treat a D-DNA and a L-DNA tetramer frame. The four monomer sequences of D-DNA and L-DNA correspond one-to-one; and the improved two-step method in Example 9 was used as the assembly method for assembly. After various enzymes were added to the D-DNA or L-DNA tetramer scaffold, they were kept in a 37° C. water bath for 17 hours, and analyzed by 2% agarose electrophoresis after sampling.

The result is shown in FIG. 9, L-DNA tetramer scaffold can withstand the treatment of four DNases without any degradation. However, D-DNA tetramers are almost completely degraded by DNAse I and S1 nucleases, and double helix structure can also be disrupted by exonuclease 1 and T7 DNA endonuclease. Therefore, L-DNA tetramer scaffold are not able to be degraded by various common DNases.

Example 11: L-DNA Frame for Assembly of Tetramers of Large Molecular Weight Proteins To demonstrate that L-DNA scaffold can also be used for the assembly of large molecular weight proteins, the L-DNA tetramer scaffold in Example 1 was used to assemble tetramer of an MBP (maltose binding protein)-anti-PDL1 single-chain antibody fusion protein (hereinafter referred to as a fusion protein having a molecular weight of 69 kDa). The MBP-anti-PDL1 single-chain antibody fusion protein was prepared as in Example 6. Four DNAs of the L-DNA tetramer scaffold were conjugated to fusion protein and purified according to the method described in Example 7 to obtain four L-DNA-fusion proteins. The buffers of the above four L-DNA-fusion proteins were replaced with phosphate buffer (50 mM $NaH_2PO_4$, 150 mM NaCl, pH 7.0), and tetramer assembly was carried out at a final concentration of 1 µM and 2 µM at 37° C. Reaction products were analyzed by 10% SDS-PAGE and molecular sieves.

The results of protein electrophoresis are shown in FIG. 10. After a fusion protein was coupled with L-DNA, its molecular weight became larger, thus the band on SDS-PAGE shifted up. At both assembly concentrations (1 µM and 2 µM), the four L-DNA-fusion proteins all specifically assembled into a fusion protein tetramer, while those unreacted fusion protein monomer (i.e., fusion protein not coupled to L-DNA) did not participate in the assembly. It indicates that L-DNA tetramer scaffold mediates the assembly of fusion protein tetramer, and the large molecular weight of the fusion protein does not affect the assembly efficiency of the L-DNA scaffold.

The molecular sieve result is shown in FIG. 11. The fusion protein tetramer eluted as a single peak and the peak shape is symmetrical, indicating that the fusion protein tetramer is very uniform and only one assembly mode exists.

Example 12: Evaluation of In Vitro Activity of Tetraspecific Antibodies Prepared Based on L-DNA Frame To analyze the in vitro activity of anti-CEA/PD-L1/CD3 tetraspecific antibody, colorectal cancer cell line LS174T (CEA positive cells) was used as a cell model. 20,000 LS174T cells were plated in 48-well plates, and after 24 hours it was stained with 3-octadecyl-2-[3-(3-octadecyl-2 (3H)-benzoxazole-2-ylidene)-1-propylene-1-yl]benzoxazole perchlorate (DiOC18, DIO cell membrane green fluorescent probe), then 400,000 PBMC (peripheral blood mononuclear cells) was added for further incubation. At the same time, a concentration gradient-diluted anti-CEA/PD-L1/CD3 tetraspecific antibody (0.001 nM-20 nM) was added and co-incubated for 96 hours. After labeling dead cells with propidium iodide (PI), the number of cells with green fluorescent probe and propidium iodide fluorescence double signal was detected by flow cytometry. Positive control was Triton-X100 treated, and Dynabeads (fine beads coupled with anti-CD28/CD3 antibody on the surface and it can efficiently activate T cells), and negative control was the buffer used for the antibody. The amount of cell death in the Triton-X100 treated group was used as 100% killing, and the buffer group was used as 0% killing.

The result is shown in FIG. 12, the anti-CEA/PD-L1/CD3 tetraspecific antibody efficiently mediated the killing of LS174T cells by T cells, and the killing activity was dose dependent. The EC50 of anti-CEA/PD-L1/CD3 tetraspecific antibody was approximately 0.7 nM.

Example 13: Ability of Anti-CEA/PD-L1/CD3 Tetraspecific Antibodies to Activate T Cells To analyze the ability of anti-CEA/PD-L1/CD3 tetraspecific antibodies to activate T cells, interferon gamma (IFN-γ) was selected as a test subject. The specific procedure was as follows: colorectal cancer cell line LS174T was used as a cell model. 20,000 LS174T cells were plated in 48-well plates, and 24 hours later, 400,000 PBMCs (peripheral blood mononuclear cells) were added for further incubation. At the same time, a concentration gradient-diluted anti-CEA/PD-L1/CD3 tetraspecific antibody (0.001 nM-20 nM) was added and co-incubated for 96 hours. IFN-γ was immobilized on the surface of T cells with Brefeldin A (Brefeldin A), and T cells were labeled with a fluorescently labeled anti-CD3 antibody, and then the number of IFN-γ/CD3 double positive cells was detected by flow cytometry. Positive control was Dynabeads (fine beads coupled with anti-CD28/CD3 antibody on the surface and it can efficiently activate T cells), and negative control was the buffer used for the antibody.

The result is shown in FIG. 13, anti-CEA/PD-L1/CD3 tetraspecific antibody of various concentrations all activated T cells to release IFN-γ, which was consistent with the results of the in vitro activity assay in Example 12. The ability of anti-CEA/PD-L1/CD3 tetraspecific antibody to activate T cells was comparable to that of the positive control (Dynabeads), while the negative control (buffer) showed no significant release of IFN-γ.

All the documents cited herein are incorporated into the invention as reference, as if each of them is individually incorporated. Further, it would be appreciated that, in light of the above described teaching of the invention, the skilled in the art could make various changes or modifications to the invention, and these equivalents would still be in the scope of the invention defined by the appended claims of the application.

The invention claimed is:

1. A protein drug library comprising three or more kinds of different protein drug monomers, each of which comprises a protein drug component moiety linked to a nucleic acid component moiety, wherein the nucleic acid component moiety of one protein drug monomer is capable of forming a double-stranded structure by complementation with the nucleic acid component moiety of at least one different protein drug monomer, thereby constituting a multimeric protein drug, wherein each protein drug monomer has a structure as shown in formula I:

P-X-L-Y-A-Z    (I);

wherein,
P is the protein drug component moiety;
X is none or a redundant peptide;
L is a linker molecule;
each of Y and Z is none or a redundant nucleic acid;
A is the nucleic acid component moiety comprising a complementary pairing region, wherein the nucleic acid component moiety is selected from the group consisting of: a L-nucleic acid, a locked nucleic acid, a 2'-fluoro-modified nucleic acid, a 5-hydroxymethylcytosine nucleic acid, and combinations thereof;
"-" is a covalent bond;
and wherein the complementary pairing region of one protein drug monomer is partially or fully complementary to the complementary pairing region of at least one different protein drug monomer.

2. The protein drug library of claim 1, wherein the protein drug component moiety is selected from the group consisting of: an antibody, a ligand of activation receptor or inhibition receptor, a biologically active enzyme, and combinations thereof.

3. The protein drug library of claim 2, wherein the antibody is for the treatment of disease selected from the group consisting of: a cancer, an autoimmune disease, an organ transplant rejection, rheumatoid arthritis, diabetes, and hemophilia.

4. A method of assembling a protein drug for personalized treatment, which comprises:
   (a) selecting at least three protein drug monomers from the protein drug library of claim 1 based on pharmaceutical information; and
   (b) mixing the at least three protein drug monomers to assemble a multispecific protein drug in a multimeric form.

5. A multimeric protein drug comprising a polymer formed by three or more kinds of different protein drug monomers,
wherein each protein drug monomer comprises a protein drug component moiety linked to a nucleic acid component moiety, wherein the nucleic acid component moiety of one protein drug monomer forms a double-stranded structure by complementation with the nucleic acid component moiety of at least one different protein drug monomer,
and wherein the nucleic acid component moiety is selected from the group consisting of: a L-nucleic acid, a locked nucleic acid, a 2'-fluoro-modified nucleic acid, a 5-hydroxymethylcytosine nucleic acid, and combinations thereof.

6. The multimeric protein drug of claim 5, wherein the protein drug component moiety is an antibody.

7. A pharmaceutical composition, which comprises:
   (i) the multimeric protein drug of claim 5 as an active ingredient; and
   (ii) a pharmaceutically acceptable carrier.

8. The protein drug library of claim 1, wherein the nucleic acid component moiety is an L-nucleic acid.

9. The multimeric protein drug of claim 5, wherein the nucleic acid component moiety is an L-nucleic acid.

10. A multimeric protein drug formed by performing the method of claim 4.

* * * * *

SEQUENCE LISTING

```
<160> NUMBER OF SEQ ID NOS: 7

<210> SEQ ID NO 1
<211> LENGTH: 42
<212> TYPE: DNA
<213> ORGANISM: Artificial sequence
<220> FEATURE:
<223> OTHER INFORMATION: L-DNA1

<400> SEQUENCE: 1
aaaacgacag tccgatgtgc caaacggctg gaagttgagc aa                        42

<210> SEQ ID NO 2
<211> LENGTH: 42
<212> TYPE: DNA
<213> ORGANISM: Artificial sequence
<220> FEATURE:
<223> OTHER INFORMATION: L-DNA2

<400> SEQUENCE: 2
aaaaggcaca tcggactgtc gaaaggcgta gcctagtgcc aa                        42

<210> SEQ ID NO 3
<211> LENGTH: 42
<212> TYPE: DNA
<213> ORGANISM: Artificial sequence
<220> FEATURE:
<223> OTHER INFORMATION: L-DNA3

<400> SEQUENCE: 3
aaaacgctga tatgcgacct gaaagctcaa cttccagccg aa                        42

<210> SEQ ID NO 4
<211> LENGTH: 42
<212> TYPE: DNA
<213> ORGANISM: Artificial sequence
<220> FEATURE:
<223> OTHER INFORMATION: L-DNA4

<400> SEQUENCE: 4
aaaacaggtc gcatatcagc gaaaggcact aggctacgcc aa                        42

<210> SEQ ID NO 5
<211> LENGTH: 239
<212> TYPE: PRT
<213> ORGANISM: Artificial sequence
<220> FEATURE:
<223> OTHER INFORMATION: Anti-PD1 single-chain antibody mutants

<400> SEQUENCE: 5

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
```

```
            50                  55                  60
Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
            100                 105                 110

Ser Ala Gly Ser Gly Gly Gly Gly Ser Gly Gly Gly Ser Gly Gly
            115                 120                 125

Gly Gly Ser Glu Ile Val Leu Thr Gln Ser Pro Ala Thr Leu Ser Leu
            130                 135                 140

Ser Pro Gly Glu Arg Ala Thr Leu Ser Cys Arg Ala Ser Gln Ser Val
145                 150                 155                 160

Ser Ser Tyr Leu Ala Trp Tyr Gln Gln Lys Pro Gly Gln Ala Pro Arg
                165                 170                 175

Leu Leu Ile Tyr Asp Ala Ser Asn Arg Ala Thr Gly Ile Pro Ala Arg
                180                 185                 190

Phe Ser Gly Ser Gly Ser Gly Thr Asp Phe Thr Leu Thr Ile Ser Ser
                195                 200                 205

Leu Glu Pro Glu Asp Phe Ala Val Tyr Tyr Cys Gln Gln Ser Ser Asn
            210                 215                 220

Trp Pro Arg Thr Phe Gly Gln Gly Thr Lys Val Glu Ile Lys Cys
225                 230                 235
```

<210> SEQ ID NO 6
<211> LENGTH: 248
<212> TYPE: PRT
<213> ORGANISM: Artificial sequence
<220> FEATURE:
<223> OTHER INFORMATION: Anti-PD-L1 single-chain antibody mutants

<400> SEQUENCE: 6

```
Gln Val Gln Leu Val Gln Ser Gly Ala Glu Val Lys Lys Pro Gly Ser
 1               5                  10                  15

Ser Val Lys Val Ser Cys Lys Thr Ser Gly Asp Thr Phe Ser Thr Tyr
                 20                  25                  30

Ala Ile Ser Trp Val Arg Gln Ala Pro Gly Gln Gly Leu Glu Trp Met
             35                  40                  45

Gly Gly Ile Ile Pro Ile Phe Gly Lys Ala His Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser Ala Gly Ser Gly Gly
            115                 120                 125

Gly Gly Ser Gly Gly Gly Gly Ser Gly Gly Gly Ser Glu Ile Val
            130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ser Tyr Leu Ala Trp
                165                 170                 175

Tyr Gln Gln Lys Pro Gly Gln Ala Pro Arg Leu Leu Ile Tyr Asp Ala
```

```
            180             185             190
Ser Asn Arg Ala Thr Gly Ile Pro Ala Arg Phe Ser Gly Ser Gly Ser
            195             200             205

Gly Thr Asp Phe Thr Leu Thr Ile Ser Ser Leu Glu Pro Glu Asp Phe
210             215             220

Ala Val Tyr Tyr Cys Gln Gln Arg Ser Asn Trp Pro Thr Phe Gly Gln
225             230             235             240

Gly Thr Lys Val Glu Ile Lys Cys
            245

<210> SEQ ID NO 7
<211> LENGTH: 247
<212> TYPE: PRT
<213> ORGANISM: Artificial sequence
<220> FEATURE:
<223> OTHER INFORMATION: Anti-CD3 single-chain antibody mutants

<400> SEQUENCE: 7

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
                20                  25                  30

Thr Met Asn Trp Val Lys Gln Ser His Gly Lys Asn Leu Glu Trp Met
            35                  40                  45

Gly Leu Ile Asn Pro Tyr Lys Gly Val Ser Thr Tyr Asn Gln Lys Phe
        50                  55                  60

Lys Asp Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Thr Leu Thr Val Phe Ser Gly Ser Gly Gly Gly Gly
            115                 120                 125

Ser Gly Gly Gly Gly Ser Gly Gly Gly Ser Asp Ile Gln Met Thr
            130                 135                 140

Gln Thr Thr Ser Ser Leu Ser Ala Ser Leu Gly Asp Arg Val Thr Ile
145                 150                 155                 160

Ser Cys Arg Ala Ser Gln Asp Ile Arg Asn Tyr Leu Asn Trp Tyr Gln
                165                 170                 175

Gln Lys Pro Asp Gly Thr Val Lys Leu Leu Ile Tyr Tyr Thr Ser Arg
            180                 185                 190

Leu His Ser Gly Val Pro Ser Lys Phe Ser Gly Ser Gly Ser Gly Thr
            195                 200                 205

Asp Tyr Ser Leu Thr Ile Ser Asn Leu Glu Gln Glu Asp Ile Ala Thr
            210                 215                 220

Tyr Phe Cys Gln Gln Gly Asn Thr Leu Pro Trp Thr Phe Ala Gly Gly
225                 230                 235                 240

Thr Lys Leu Glu Ile Lys Cys
            245
```